(12) United States Patent
Ogihara et al.

(10) Patent No.: US 10,458,941 B2
(45) Date of Patent: Oct. 29, 2019

(54) ELECTROCHEMICAL MEASUREMENT DEVICE AND ELECTROCHEMICAL MEASUREMENT APPARATUS PROVIDED WITH ELECTROCHEMICAL MEASUREMENT DEVICE

(71) Applicant: Panasonic Intellectual Property Management Co., Ltd., Osaka (JP)

(72) Inventors: Jun Ogihara, Mie (JP); Sumihiro Otsuka, Mie (JP); Noriteru Furumoto, Mie (JP); Masahiro Yasumi, Osaka (JP); Atsushi Shunori, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 126 days.

(21) Appl. No.: 15/606,553

(22) Filed: May 26, 2017

(65) Prior Publication Data

US 2017/0261460 A1    Sep. 14, 2017

Related U.S. Application Data

(63) Continuation of application No. PCT/JP2015/006061, filed on Dec. 7, 2015.

(30) Foreign Application Priority Data

Dec. 12, 2014 (JP) .................. 2014-251393

(51) Int. Cl.
*G01N 27/28* (2006.01)
*G01N 27/416* (2006.01)
*G01N 33/483* (2006.01)

(52) U.S. Cl.
CPC ......... *G01N 27/283* (2013.01); *G01N 27/416* (2013.01); *G01N 33/4833* (2013.01)

(58) Field of Classification Search
CPC ............ G01N 27/403; G01N 27/327; G01N 27/3272; G01N 27/3275; G01N 33/48728;
(Continued)

(56) References Cited

U.S. PATENT DOCUMENTS 4,571,292 A * 2/1986 Liu .............. G01N 27/404
                                                204/412
6,990,367 B2 * 1/2006 Kiser ............ A61B 5/14532
                                                600/345
(Continued)

FOREIGN PATENT DOCUMENTS

| CN | 102395879 A | 3/2012 |
| JP | 2010-121948 | 6/2010 |
| WO | 2014/073195 | 5/2014 |

OTHER PUBLICATIONS

Date et al. "Monitoring oxygen consumption of single mouse embryos using an integrated electrochemical microdevice" Biosensors and Bioelectronics, vol. 30, Issue 1, p. 100-106, Dec. 15, 2011 (Year: 2011).*

(Continued)

*Primary Examiner* — Susan D Leong
(74) *Attorney, Agent, or Firm* — McDermott Will & Emery LLP

(57) ABSTRACT

Provided is an electrochemical measurement device capable of measuring more accurately and an electrochemical measurement apparatus provided with the electrochemical measurement device. The electrochemical measurement device includes a base part, and a placement part on which an object to be measured is placed, the placement part being provided to the base part. The electrochemical measurement device also includes an electrode part provided near the placement part on the base part, a wiring part provided on a surface of the base part and electrically connected to the electrode part, (Continued)

and an insulator that covers the wiring part. Further, a protruding part is provided on the base part of the electrochemical measurement device so as to protrude past the insulator.

8 Claims, 11 Drawing Sheets

(58) Field of Classification Search
CPC .............. G01N 33/48; G01N 33/487; G01N 33/48785; G01N 33/50; G01N 33/5005
See application file for complete search history.

(56) References Cited

U.S. PATENT DOCUMENTS

| | | | |
|---|---|---|---|
| 2005/0014129 A1* | 1/2005 | Cliffel | G01N 33/5005 435/4 |
| 2005/0173249 A1* | 8/2005 | Barlow | B01J 19/0046 204/601 |
| 2006/0246490 A1* | 11/2006 | Anderson | B01F 11/0071 435/6.11 |
| 2012/0036921 A1 | 2/2012 | De Coulon et al. | |
| 2012/0137797 A1* | 6/2012 | Sawamura | B01L 3/5085 73/866 |
| 2013/0230881 A1* | 9/2013 | Yasuda | G01N 33/5088 435/29 |
| 2015/0125942 A1* | 5/2015 | Grier, Jr. | C12M 23/00 435/288.4 |
| 2015/0260675 A1 | 9/2015 | Nakatani et al. | |

OTHER PUBLICATIONS

International Search Report of PCT application No. PCT/JP2015/006061 dated Jan. 12, 2016.

English Translation of Chinese Search Report dated Oct. 31, 2018 for the related Chinese Patent Application No. 201580065357.0.

* cited by examiner

ELECTROCHEMICAL MEASUREMENT DEVICE AND ELECTROCHEMICAL MEASUREMENT APPARATUS PROVIDED WITH ELECTROCHEMICAL MEASUREMENT DEVICE

BACKGROUND

1. Technical Field

The present disclosure relates to an electrochemical measurement device and an electrochemical measurement apparatus provided with the electrochemical measurement device.

2. Description of the Related Art

A biological sample (object to be measured) which is a cell such as a fertilized egg and a tissue is active by transporting various substances between inside and outside thereof. For example, a cardiac muscle cell enables information transmission based on electric signals or compounds by transporting K ions, Na ions, Ca ions, etc., thereby controlling pulsation of a heart. In addition, a fertilized egg incorporates oxygen around thereof into cells by respiration, and is cleaved in a follicle while consuming incorporated oxygen. As a unit for measuring such an activity condition of a biological sample, methods have been known for electrically measuring a physicochemical state change occurring around a biological sample being held on an electrochemical measurement device. These methods are used for a pharmacological test for drug candidate compounds using model cells, or as a method for testing an activity of a fertilized egg.

For example, there has been a method, as a method for measuring respiration activity of a fertilized egg, in which a fertilized egg is caught by a micromanipulator or a micropipette, and an oxygen concentration around the fertilized egg is electrochemically measured using a working electrode (electrode). By using this method, the respiration activity of the fertilized egg can be quantified.

The above-mentioned electrochemical measurement method is configured based on a scanning electrochemical microscopy (SECM), and therefore, this method needs an operation to bring a working electrode (electrode) of a probe close to a biological sample, such as a fertilized egg, as an object to be measured. However, the operation for the working electrode (electrode) needs to be carried out manually, and thus, there is a problem in operability such that variation is caused depending on skills of operators.

As a unit for improving operability, a planar electrochemical measurement device has been known which has a micro working electrode (electrode) mounted on a substrate (see PTL 1, for example).

In PTL 1, the electrochemical measurement device includes a substrate, a placement part which is provided to the substrate and on which a biological sample (object to be measured) is placed, an electrode provided near the placement part, and an insulating film that covers the surface of the substrate so that the electrode is exposed. A peripheral wall part is provided around the substrate in the electrochemical measurement device to implement an electrochemical measurement apparatus having a space (well) for holding solution therein.

When a fertilized egg (object to be measured) is placed on the placement part of the electrochemical measurement apparatus, the fertilized egg is located near the electrode, whereby an oxygen concentration around the fertilized egg can electrochemically be measured with ease, and thus, the respiration activity of the fertilized egg can easily be quantified.

CITATION LIST

Patent Literature

PTL 1: Unexamined Japanese Patent Publication No. 2010-121948

SUMMARY

The present disclosure aims to provide an electrochemical measurement device capable of measuring more accurately and an electrochemical measurement apparatus provided with the electrochemical measurement device.

The electrochemical measurement device according to the present disclosure includes: a base part; a placement part on which an object to be measured is placed, the placement part being provided to the base part; an electrode part provided near the placement part on the base part; a wiring part provided to a surface of the base part and electrically connected to the electrode part; an insulator that covers the wiring part; and a protruding part provided to the base part so as to protrude past the insulator.

The present disclosure can provide an electrochemical measurement device capable of measuring more accurately and an electrochemical measurement apparatus provided with the electrochemical measurement device.

DETAILED DESCRIPTION

Prior to the description of the exemplary embodiments of the invention in the present disclosure, problems involved with a conventional technology will be described below.

Figure 14:
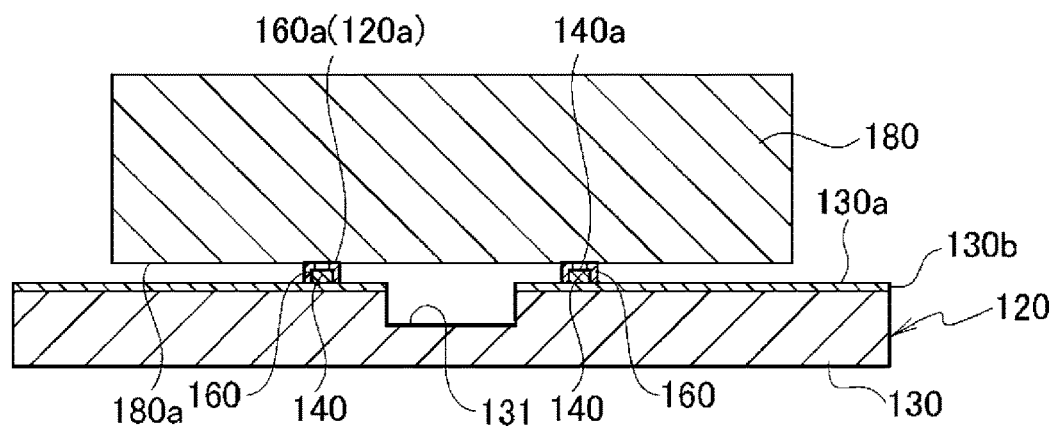
FIG. 14 schematically illustrates a method for manufacturing a conventional electrochemical measurement apparatus, and is a sectional view illustrating a state in which a pin is pressed against an upper part of an electrochemical measurement device.
Figure 15:
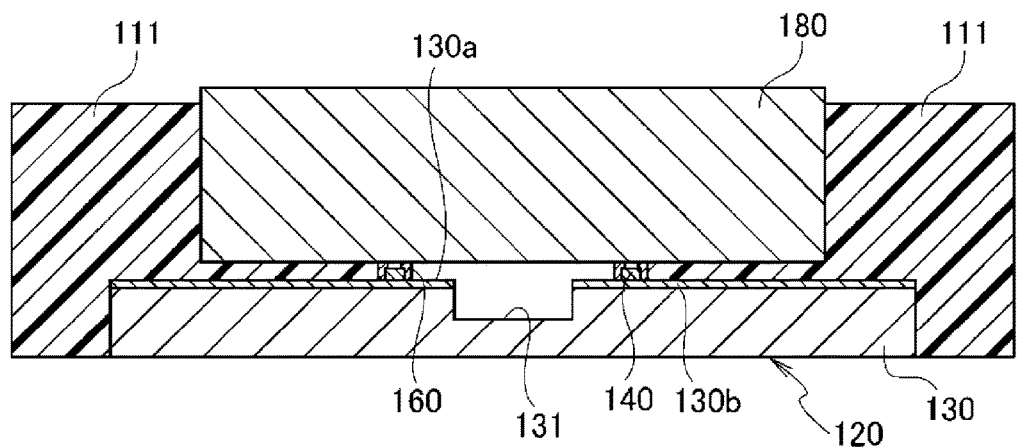
FIG. 15 schematically illustrates the method for manufacturing the conventional electrochemical measurement apparatus, and is a sectional view illustrating a state in which a pin is pressed against the upper part of the electrochemical measurement apparatus to form a peripheral wall part on a peripheral portion of the electrochemical measurement device.
Figure 16:
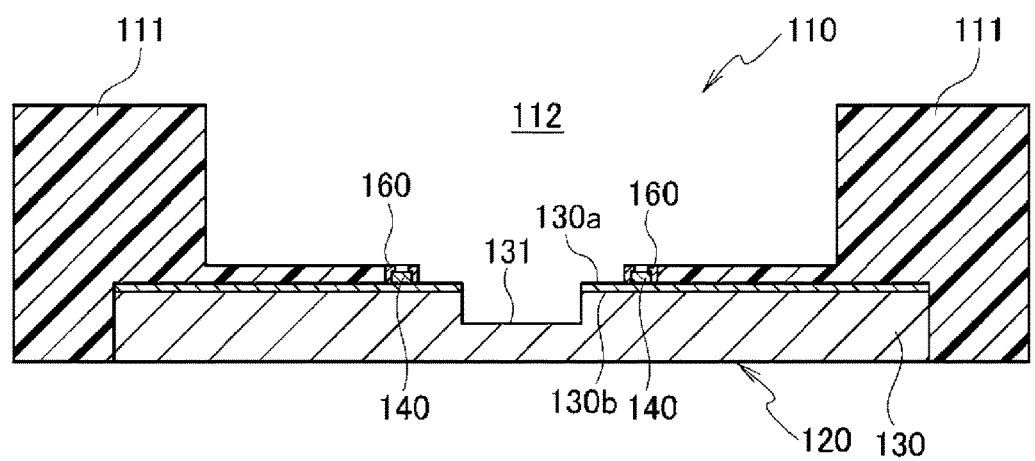
FIG. 16 schematically illustrates the method for manufacturing the conventional electrochemical measurement apparatus, and is a sectional view illustrating a state in which the electrochemical measurement apparatus is formed by removing the pin.

To simply manufacture a conventional electrochemical measurement apparatus, a method illustrated in FIGS. 14 to 16 is generally applied.

Specifically, at first, placement part 131 and electrode 140 are formed on surface 130a of substrate 130 having insulating film 130b formed thereon, and electrode 140 is covered by insulator 160 so that at least a portion of surface 140a of electrode 140 is exposed. Thus, electrochemical measurement device 120 is formed.

Next, pin 180 is put on surface 120a of electrochemical measurement device 120 (see FIG. 14). At that time, pin 180 is put so that lower surface 180a of pin 180 is brought into contact with surface 160a of insulator 160. Therefore, in the state illustrated in FIG. 14, pin 180 is pressed against insulator 160.

Next, with pin 180 being pressed against insulator 160, resin is poured around substrate 130 and pin 180 to form peripheral wall part 111 around substrate 130 (see FIG. 15). Note that peripheral wall part 111 is formed by using a die not illustrated.

Then, pin 180 is removed, and thus, electrochemical measurement apparatus 110 having well 112 for holding solution is formed (see FIG. 16).

However, with the above-mentioned conventional method, peripheral wall part 111 is formed with insulator 160 being pressed by pin 180. Therefore, during the formation of electrochemical measurement apparatus 110, large external force is applied on insulator 160, which might cause damage on insulator 160. If insulator 160 is damaged, a desired electric signal cannot be obtained, resulting in that accurate measurement cannot be achieved in some cases.

As described above, there is apprehension that the conventional technology is incapable of measuring accurately.

The exemplary embodiments of the invention according to the present disclosure will be described below with reference to the drawings.

Hereinafter, those used for examination and analysis of an activity state of a biological sample, which is a cell such as a fertilized egg or a tissue, will be described as an example of an electrochemical measurement device and an electrochemical measurement apparatus. In addition, in the description below, a top-bottom direction is defined with a state in which a substrate is disposed with the surface thereof facing upward.

Further, multiple exemplary embodiments described below include similar components. Therefore, the similar components are identified by the same reference marks, and the redundant description will not be repeated below.

First Exemplary Embodiment

Figure 1:
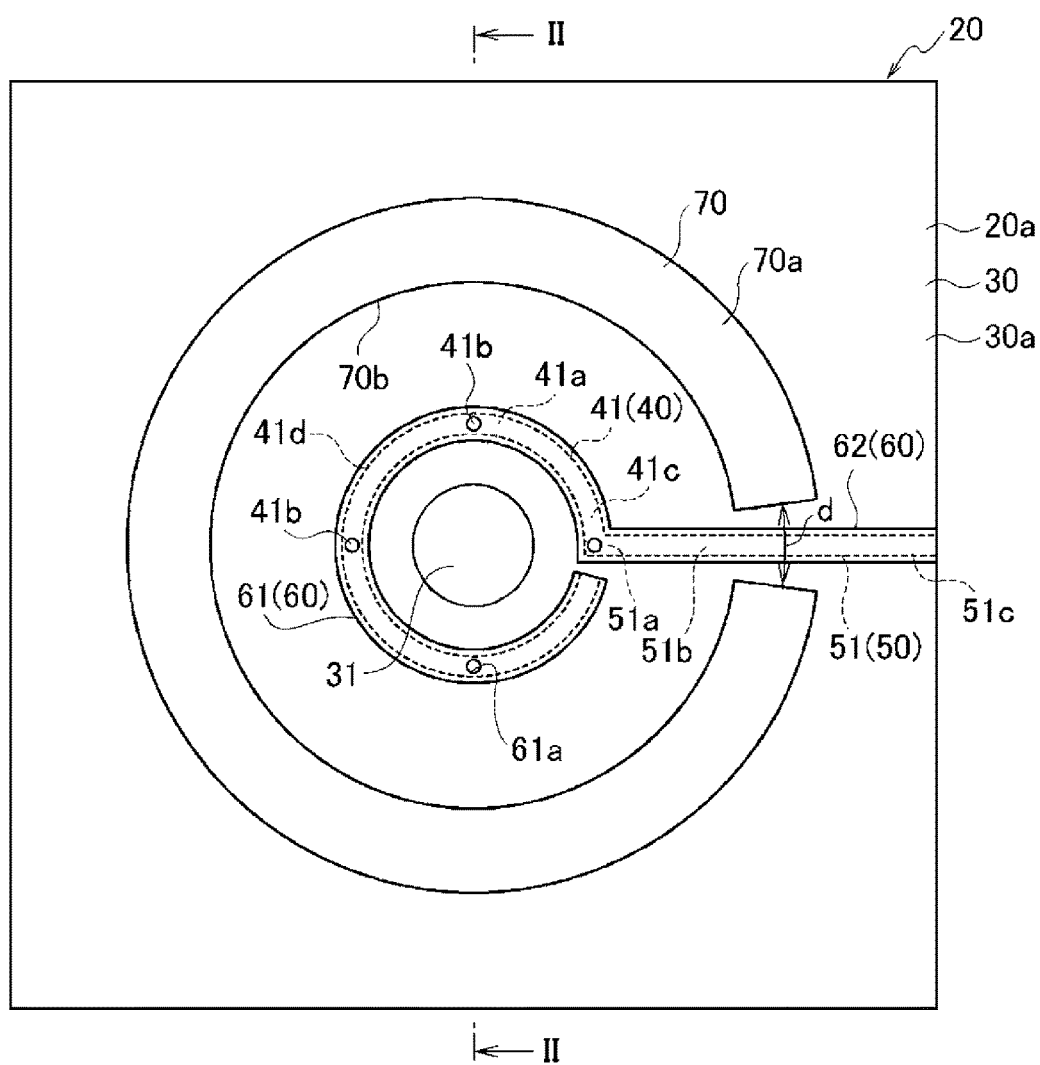
FIG. 1 is a top view illustrating an electrochemical measurement device according to a first exemplary embodiment of the present disclosure.
Figure 2:
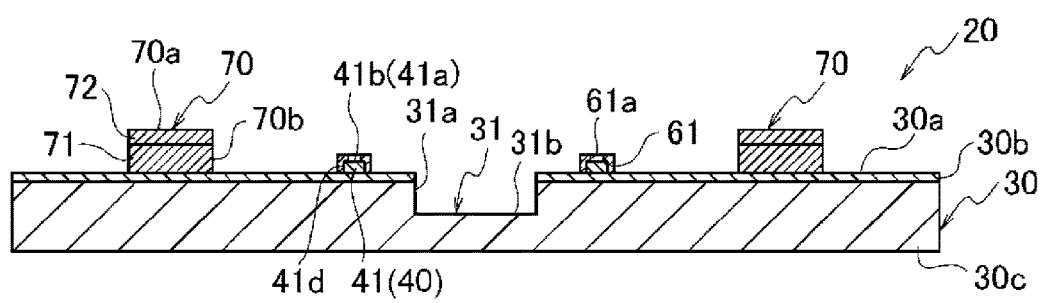
FIG. 2 is a sectional view taken along line II-II in FIG. 1.

As illustrated in FIGS. 1 and 2, electrochemical measurement device (electrochemical measurement device for biological sample measurement) 20 includes substrate (base part) 30, and sample placement part (placement part) 31 which is provided to substrate (base part) 30 and on which a biological sample (object to be measured) can be placed. FIG. 1 is a top view of electrochemical measurement device 20. FIG. 2 is a sectional view taken along line II-II in FIG. 1.

Substrate 30 is formed into substantially a rectangle, and can be made of glass, resin, silicon, ceramics, etc. (the present exemplary embodiment shows substrate 30 made of silicon). Notably, substrate 30 is not limited to have a rectangular shape, and may have a variety of shapes such as a circle or a polygon. In addition, the base part is not limited to a plate-shaped substrate, and may have any shape, so long as it allows sample placement part 31 to be formed thereon and has a surface on which later-described electrode 40 is to be formed.

Sample placement part 31 can be a recess formed on surface 30a of substrate 30, for example. The recess can be formed to have a columnar shape or a polygonal column, for example. In the present exemplary embodiment, a columnar recess is formed on substantially the center of surface 30a of substrate 30 to form sample placement part 31 on substrate 30, as illustrated in FIGS. 1 and 2.

The depth of sample placement part 31 is preferably a half of or less than the height of a biological sample. If the depth of sample placement part 31 is set to be a half of or less than the height of a biological sample as described above, the biological sample is exposed from sample placement part 31, so that a physicochemical state change such as oxygen concentration is easy to be detected by electrode part 40. It is to be noted that the depth of sample placement part 31 can freely be set according to the size of the biological sample, and is not limited to be a half of or lower than the height of the biological sample.

In addition, wall face 31a of sample placement part 31 and bottom surface 31b of sample placement part 31 are preferably subjected to a hydrophilic treatment. With this treatment, wall face 31a and bottom surface 31b of sample placement part 31 are given hydrophilic property, whereby solution can easily be injected into sample placement part 31 to prevent remnants of air bubbles or the like. The hydrophilic treatment for wall face 31a and bottom surface 31b can be carried out by an ashing process, for example.

It can also be configured such that the wall face of the sample placement part is tapered at an angle from 90° to 180° inclusive with respect to the bottom surface so as to allow a biological sample to be more securely fixed. In addition, the shape of the sample placement part may be formed into a circular cone or a polygon so as to allow a biological sample to be more securely fixed.

Electrochemical measurement device 20 also includes electrode part 40 which is provided near sample placement part (placement part) 31 on substrate (base part) 30 and protrudes from substrate 30. It is only necessary that at least a portion of electrode part 40 is provided near sample placement part (placement part) 31 on substrate (base part) 30, and it is unnecessary to provide the entire electrode part near sample placement part (placement part) 31 on substrate (base part) 30.

Note that, if substrate 30 is a conductor or a semiconductor, an insulating layer is preferably provided between substrate 30 and electrode part 40. The insulating layer can be made of silicon dioxide, silicon nitride, organic compound, etc. In the present exemplary embodiment, a silicon substrate is used as substrate 30, and insulating part 30b made of silicon dioxide is formed on surface 30a of substrate 30. Due to insulating part 30b, electrode part 40 and substrate body 30c are insulated from each other.

In the present exemplary embodiment, as electrode part 40, first ring electrode 41 with substantially a C shape in a plan view is provided on surface 30a of substrate 30 to surround sample placement part 31. It is preferable that first ring electrode 41 is concentrically arranged around sample placement part 31. It is to be noted that, while the present exemplary embodiment describes first ring electrode 41 which has a ring shape having a gap on a portion thereof, first ring electrode 41 may have almost an O shape with no gap.

First ring electrode 41 can be made of noble metals such as platinum, gold, or silver, for example. In addition, first ring electrode 41 can be made of a material popularly used as an electrode material for a battery, such as carbon or lithium cobalt oxide. That is, the material for first ring electrode 41 can be selected, as appropriate, in consideration of a composition of culture solution or voltage and current required for the measurement.

Electrochemical measurement device 20 also includes wiring part 50 which is provided on surface 30a of substrate (base part) 30 and electrically connected to electrode part 40.

In the present exemplary embodiment, first electrode exposed part 51a located on one end of wiring pattern 51 is connected to one end 41c of first ring electrode 41 formed into a C shape, and wiring pattern 51 linearly extends toward the side opposite to sample placement part 31 (extends radially outward of sample placement part 31) from first electrode exposed part 51a. Note that the shape of wiring pattern 51 is not limited to be linear.

Electrochemical measurement device 20 also includes insulator 60 for covering a region (surface 51b and lateral surface 51c) of wiring part 50 exposed from substrate 30.

Insulator 60 has first insulating layer 61 for covering a region (surface 41a and lateral surface 41d) of first ring electrode 41 exposed from substrate 30 and second insulating layer 62 for covering the region (surface 51b and lateral surface 51c) of wiring pattern 51 exposed from substrate 30. In addition, in the present exemplary embodiment, first insulating layer 61 and second insulating layer 62 are integrally formed. Specifically, the region of first ring electrode 41 exposed from substrate 30 and the region of wiring pattern 51 exposed from substrate 30 are covered by single insulator 60.

First insulating layer 61 is formed on surface 30a of substrate 30 so as to cover first ring electrode 41, and made of silicon dioxide, silicon nitride, organic compound, or the like to insulate first ring electrode 41 and culture solution from each other.

Similarly, second insulating layer 62 is formed on surface 30a of substrate 30 so as to cover wiring pattern 51, and made of silicon dioxide, silicon nitride, organic compound, or the like to insulate wiring pattern 51 and culture solution from each other.

In addition, in the present exemplary embodiment, opening 61a is formed on first insulating layer 61. The region of first ring electrode 41 exposed from substrate 30, that is, a portion (a portion of surface 41a in the present exemplary embodiment) of the region (surface 41a and lateral surface 41d) exposed from substrate 30 when first ring electrode 41 is not covered by first insulating layer 61, is exposed through opening 61a.

Specifically, first ring electrode 41 has first electrode exposed part 41b exposed from opening 61a in first insulating layer 61. According to this configuration, first ring electrode 41 is in contact with culture solution at first electrode exposed part 41b. Note that opening 61a in first insulating layer 61 can be formed to have a circular shape or a polygonal shape, for example (in FIG. 1, circular opening 61a is illustrated).

As described above, due to the configuration in which first ring electrode 41 is covered by first insulating layer 61 so that first ring electrode 41 is in contact with the culture solution only at first electrode exposed part 41b, reduction in noise can be achieved, whereby more accurate electrochemical measurement can be implemented.

In addition, in the present exemplary embodiment, wiring pattern 51 drawn from first ring electrode 41 is covered by second insulating layer 62, by which the contact between wiring pattern 51 and the culture solution can be prevented. According to this configuration, current detection on an unnecessary position based on an electrochemical reaction can be reduced.

If electrochemical measurement is carried out by bringing first ring electrode 41 entirely in contact with culture solution without being covered by first insulating layer 61, nonfaradaic current being noise increases with an increase in the electrode area, by which accurate electrochemical measurement cannot be carried out in some cases. Further, in measurement of dissolved oxygen in culture solution due to respiration activity of a fertilized egg, for example, an amount of oxygen consumed in response to an electrochemical reaction increases with an increase in the electrode area, which might affect the oxygen concentration near the fertilized egg, and thus, the respiration activity cannot accurately be measured in some cases.

Therefore, it is preferable that the area of first electrode exposed part 41b is set to be 500 µm$^2$ or less so that nonfaradaic current being measurement noise is reduced or the influence on the oxygen concentration near the fertilized egg caused by the consumption of oxygen in response to the electrochemical reaction is reduced.

In addition, in the present exemplary embodiment, a plurality of first electrode exposed parts 41b is arranged on first ring electrode 41 to enable multidirectional measurement of a biological sample. In this case, it is preferable that first electrode exposed parts 41b are arranged to be equally distant from sample placement part 31. With this configuration, a physicochemical state change such as an oxygen concentration around a biological sample can be easily measured by electrochemical measurement, regardless of imbalance in the activity of the biological sample.

In the present exemplary embodiment, four first electrode exposed parts 41b are provided on first ring electrode 41. Four first electrode exposed parts 41b are equally spaced at 90 degrees around sample placement part 31. Note that the number of first electrode exposed parts 41b is not limited to four. For example, eight first exposed electrode parts 41b can be formed on first ring electrode 41. In this case, first exposed electrode parts 41b are equally spaced at 45 degrees around sample placement part 31.

In addition, first electrode exposed parts 41b are preferably arranged such that an effect caused by overlapping of diffusion layers formed by respective first electrode exposed parts 41b is not exerted on the electrochemical reaction occurring on first electrode exposed parts 41b. For example, the distance between two adjacent first electrode exposed parts 41b is preferably 6.5 times or more the dimension of first electrode exposed part 41b.

Herein, the dimension of first electrode exposed part 41b indicates a diameter of a minimum circle which includes first electrode exposed part 41b. For example, if first electrode exposed part 41b is a circle, the dimension of first electrode exposed part 41b is a diameter. If first electrode exposed part 41b is a rectangle, the dimension of first electrode exposed part 41b is the length of a diagonal.

In addition, first electrode exposed parts 41b are arranged to be equally distant from the center of sample placement part 31. With the configuration in which first electrode exposed parts 41b are arranged to be equally distant from sample placement part 31, a physicochemical state change such as an oxygen concentration around a biological sample can be easily measured by electrochemical measurement, regardless of imbalance in the activity of the biological sample.

In the present exemplary embodiment, pressure-receiving part (protruding part) 70 protruding past insulator 60 (second insulator 62) is provided on surface 30a of substrate (base part) 30. Pressure-receiving part 70 is pressed by pin 80 when peripheral wall part 11 of electrochemical measurement apparatus 10 to be described later is to be formed.

In the present exemplary embodiment, pressure-receiving part 70 is provided on a region, not having electrode part 40 formed thereon, on surface 30a of substrate 30, as illustrated in FIG. 1.

In addition, pressure-receiving part 70 is formed to surround placement part 31, and also formed to surround electrode part 40 (first ring electrode 41). According to this configuration, in forming peripheral wall part 11 of electrochemical measurement apparatus 10, molten resin is prevented from flowing toward placement part 31 or electrode part 40 (first ring electrode 41).

Specifically, pressure-receiving part 70 is formed into substantially a C shape in a plan view, and gap d is formed on a disconnected part. Wiring pattern 51 (wiring part 50) covered by second insulating layer 62 is present in gap d. In other words, pressure-receiving part 70 is formed on both sides of wiring pattern 51 (wiring part 50). Notably, gap d is set to have a size for preventing resin for forming peripheral wall part 11 from flowing toward placement part 31 or electrode part 40 (first ring electrode 41) through gap d, in consideration of viscosity or the like of the resin.

It is preferable that pressure-receiving part 70 is also concentrically arranged around sample placement part 31.

When first ring electrode 41 and pressure-receiving part 70 are concentrically arranged around sample placement part 31 as described above, the surface (lateral surface 70b) of pressure-receiving part 70 facing electrode part 40 is along the surface (lateral surface 41d) of electrode part 40 facing pressure-receiving part 70.

In addition, pressure-receiving part 70 can be configured to include a portion made of a material same as the material for insulator 60. For example, to simplify a manufacturing process, layer 71 of pressure-receiving part 70 facing substrate 30 can be formed simultaneously with the formation of insulator 60 on surface 30a of substrate 30 (see FIG. 2). Note that upper layer 72 of pressure-receiving part 70 may be formed from the same material as insulator 60 or from a material different from the material for insulator 60. If upper layer 72 is formed from a material different from the material for insulator 60 as described above, pressure-receiving part 70 includes a portion formed from a material different from the material for insulator 60. Note that the entire of pressure-receiving part 70 may be formed from a material different from the material for insulator 60.

Various materials such as resin or metal can be used for forming pressure-receiving part 70. Materials having chemical durability, materials which are difficult to be oxidized, materials having mechanical durability, etc. can be selected as appropriate according to usage.

When the outer perimeter or the peripheral portion of substrate 30 is enclosed by peripheral wall part 11 by using electrochemical measurement device 20 having the above-mentioned configuration, electrochemical measurement apparatus 10 having well 12 formed in peripheral wall part 11 can be obtained. Peripheral wall part 11 can be formed from glass, resin, silicon, ceramics, silicon rubber, etc., for example.

Figure 3:
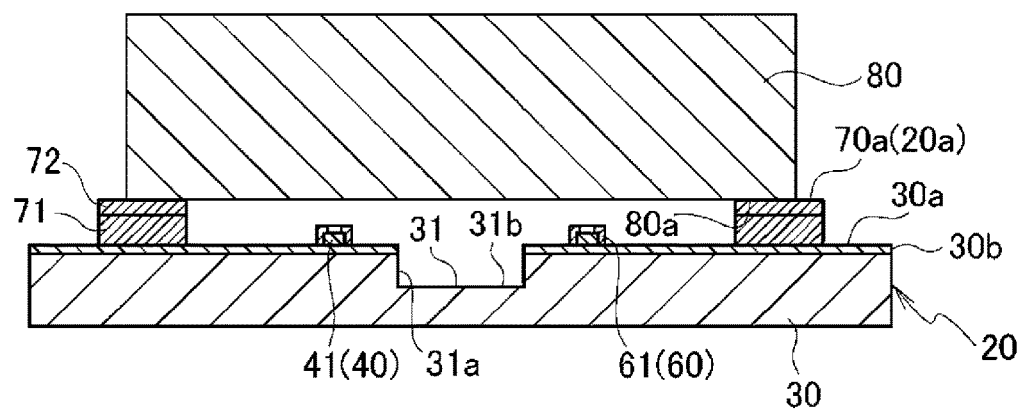
FIG. 3 schematically illustrates a method for manufacturing an electrochemical measurement apparatus according to the first exemplary embodiment of the present disclosure, and is a sectional view illustrating a state in which a pin is pressed against an upper part of the electrochemical measurement device.
Figure 4:
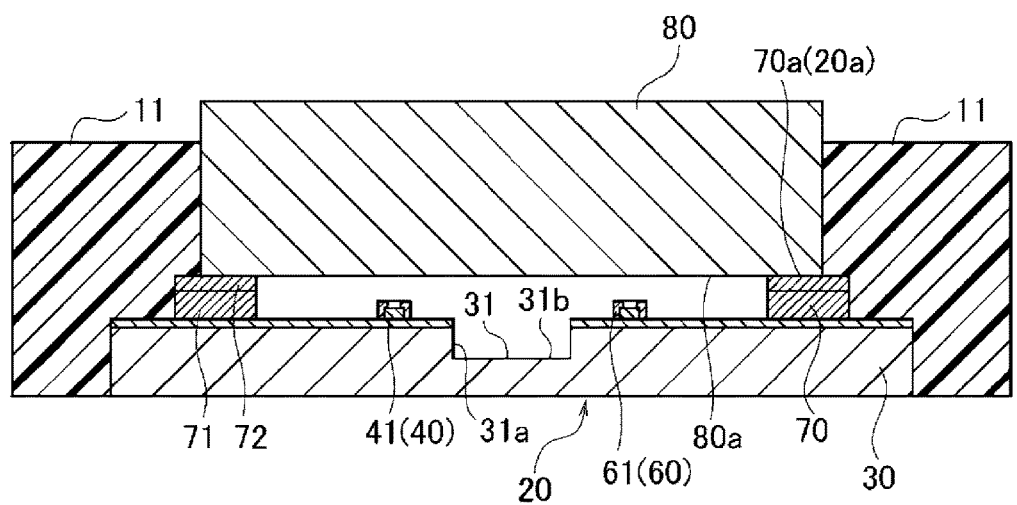
FIG. 4 schematically illustrates the method for manufacturing the electrochemical measurement apparatus according to the first exemplary embodiment of the present disclosure, and is a sectional view illustrating a state in which a pin is pressed against the upper part of the electrochemical measurement apparatus to form a peripheral wall part on a peripheral portion of the electrochemical measurement device.
Figure 5:
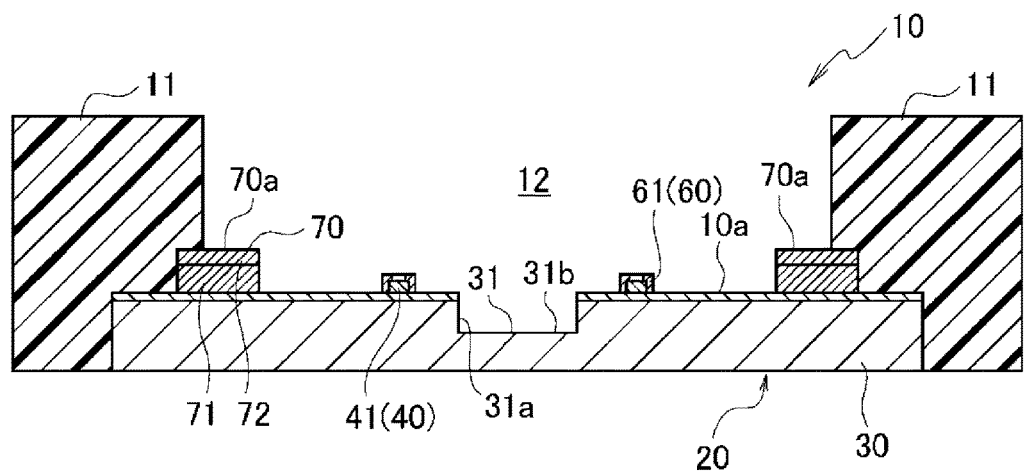
FIG. 5 schematically illustrates the method for manufacturing the electrochemical measurement apparatus according to the first exemplary embodiment of the present disclosure, and is a sectional view illustrating a state in which the electrochemical measurement apparatus is formed by removing the pin.

Now, one example of a method for forming electrochemical measurement apparatus 10 using electrochemical measurement device 20 will be described with reference to FIGS. 3 to 5. FIGS. 3 to 5 are views schematically illustrating the method for manufacturing electrochemical measurement apparatus 10. FIG. 3 is a sectional view illustrating a state in which a pin is pressed against an upper part of the electrochemical measurement device. FIG. 4 is a sectional view illustrating a state in which the pin is pressed against the upper part of the electrochemical measurement device to form a peripheral wall part on a peripheral portion of the electrochemical measurement device. FIG. 5 is a sectional view illustrating a state in which the electrochemical measurement apparatus is formed by removing the pin.

Firstly, electrochemical measurement device 20 having the above-mentioned configuration is formed.

Next, pin 80 is put on surface 20a of electrochemical measurement device 20 (see FIG. 3). At that time, pin 80 is put so that lower surface 80a of pin 80 is brought into contact with surface 70a of pressure-receiving part 70. Thus, in the state illustrated in FIG. 3, insulator 60 is not pressed by pin 80, but pressure-receiving part 70 is pressed by pin 80.

Next, with pin 80 being pressed against pressure-receiving part 70, resin is poured around substrate 30 and pin 80 to form peripheral wall part 11 around substrate 30 (see FIG. 4). Note that peripheral wall part 11 is formed by using a die not illustrated.

Then, pin 80 is removed, and thus, electrochemical measurement apparatus 10 having well 12 for holding solution (culture solution, or the like) is formed (see FIG. 5).

Specifically, electrochemical measurement apparatus 10 according to the present exemplary embodiment includes electrochemical measurement device 20, and peripheral wall part 11 that surrounds electrochemical measurement device 20 so that the surface of electrochemical measurement device 20 on which sample placement part 31 is formed becomes bottom surface 10a.

While pressure-receiving part 70 formed into substantially a C shape in a plan view is illustrated in the present exemplary embodiment, the shape of pressure-receiving part 70 is not limited thereto. Examples of the shape of pressure-receiving part 70 will be described below as modifications.

First Modification

Figure 6:
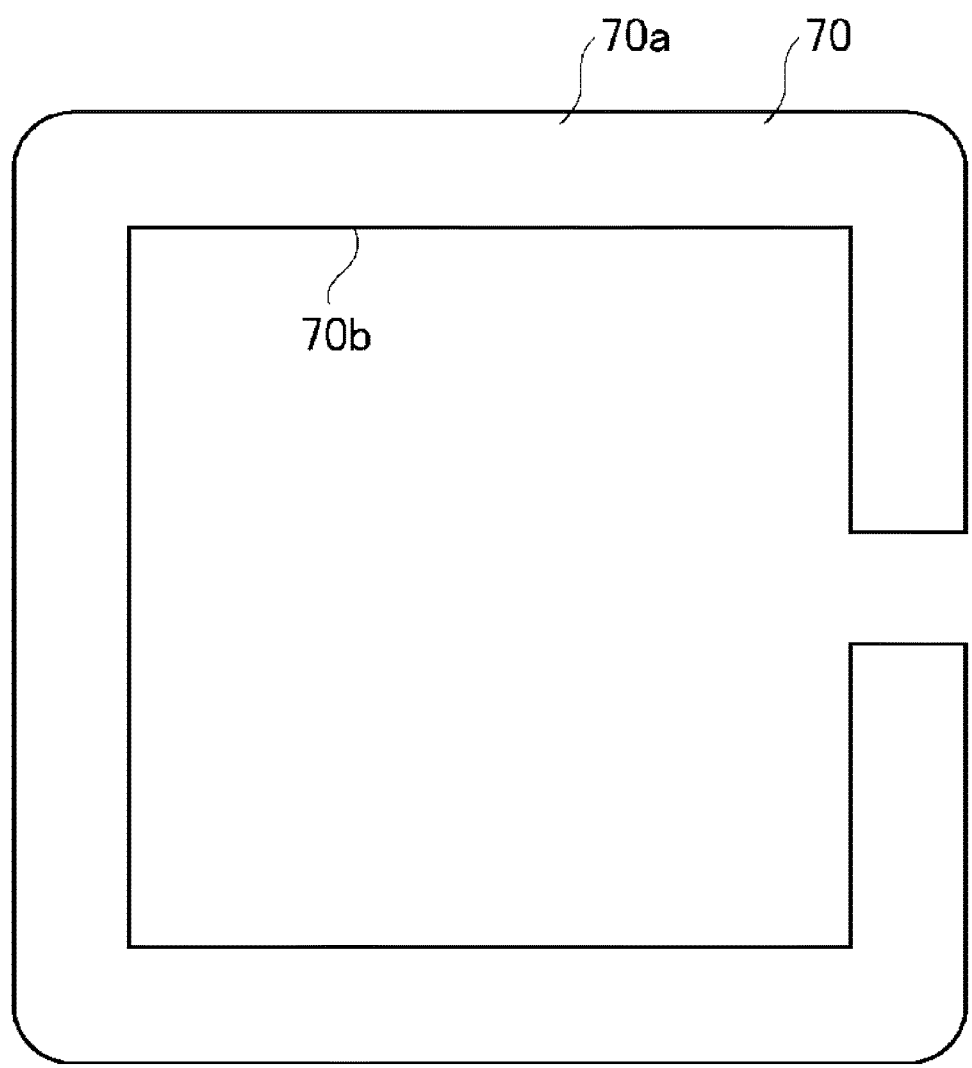
FIG. 6 is a top view illustrating a protruding part according to a first modification of the first exemplary embodiment of the present disclosure.

For example, pressure-receiving part (protruding part) 70 may be formed into substantially a rectangle in a plan view as illustrated in a top view in FIG. 6. When being formed into substantially a rectangle as described above, pressure-receiving part (protruding part) 70 can be formed to have a shape along rectangular substrate 30.

Second Modification

Figure 7:
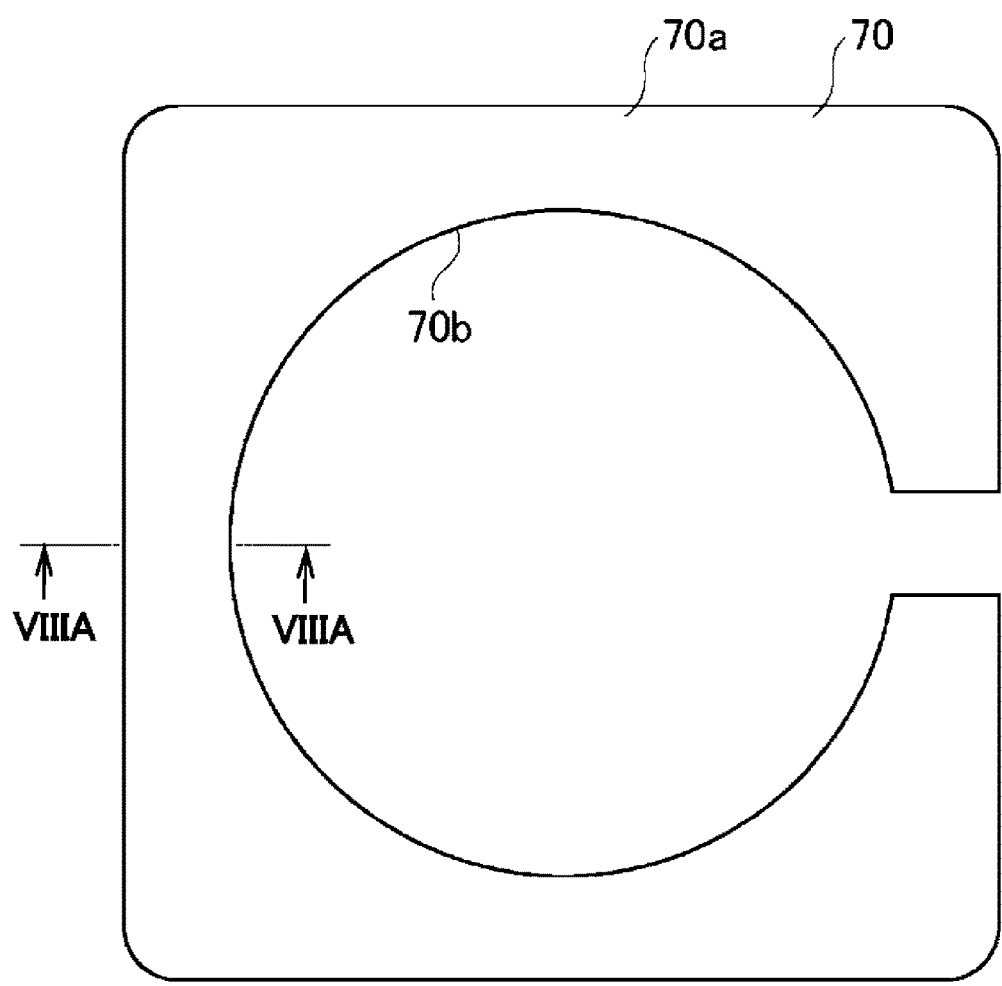
FIG. 7 is a top view illustrating a protruding part according to a second modification of the first exemplary embodiment of the present disclosure.

In addition, as illustrated in a top view in FIG. 7, pressure-receiving part 70 can be configured such that, in a plan view, the inner peripheral contour thereof is formed into a circle and the outer peripheral contour thereof is formed into a rectangle. According to this configuration, the area (contact area with lower surface 80a of pin 80) of surface 70a of pressure-receiving part 70 can be increased, while surface (lateral surface 70b) of pressure-receiving part 70 facing electrode part 40 is formed along surface (lateral surface 41d) of electrode part 40 facing pressure-receiving part 70.

Figure 8A:
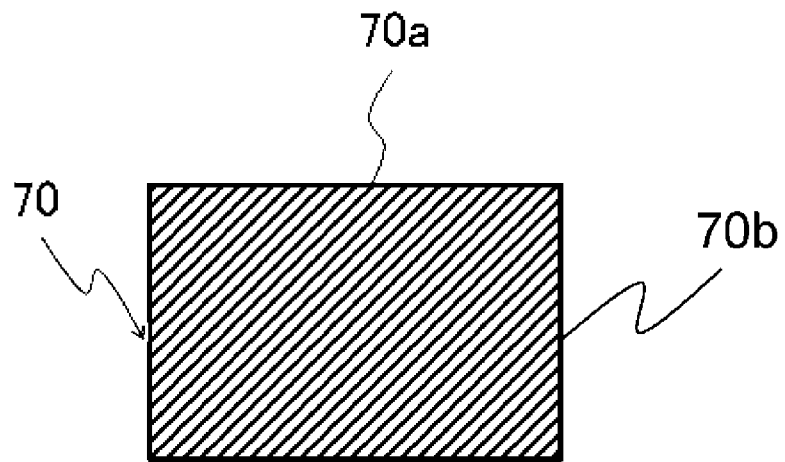
FIG. 8A is a sectional view, taken along line VIIIA-VIIIA in FIG. 7, illustrating a protruding part according to a modification of the first exemplary embodiment of the present disclosure.

FIG. 8A illustrates a sectional view of pressure-receiving part 70 according to the second modification. This sectional view illustrates a cross-part taken along line VIIIA-VIIIA in FIG. 7. In FIG. 8A, surface 70a of pressure-receiving part 70 is flat.

Third Modification

Figure 8B:
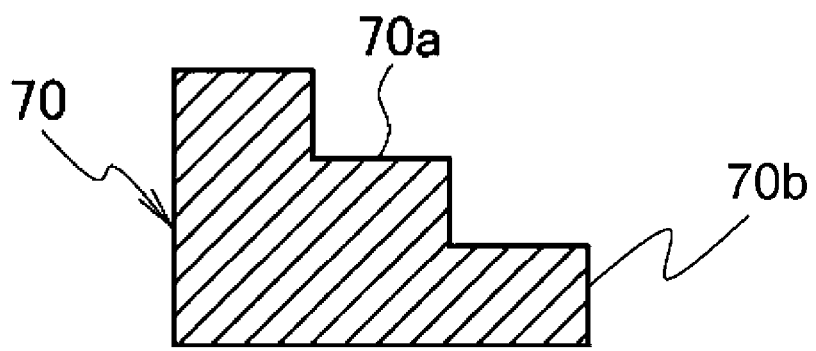
FIG. 8B is a sectional view, corresponding to the VIIIA-VIIIA sectional view in FIG. 8A, illustrating a protruding part according to a third modification of the first exemplary embodiment of the present disclosure.

The second modification describes the configuration in which surface 70a of pressure-receiving part 70 is flat as illustrated in FIG. 8A. However, the shape of pressure-receiving part 70 is not limited thereto. For example, surface 70a may have a stepped part as illustrated in a sectional view in FIG. 8B.

Fourth Modification

Figure 8C:
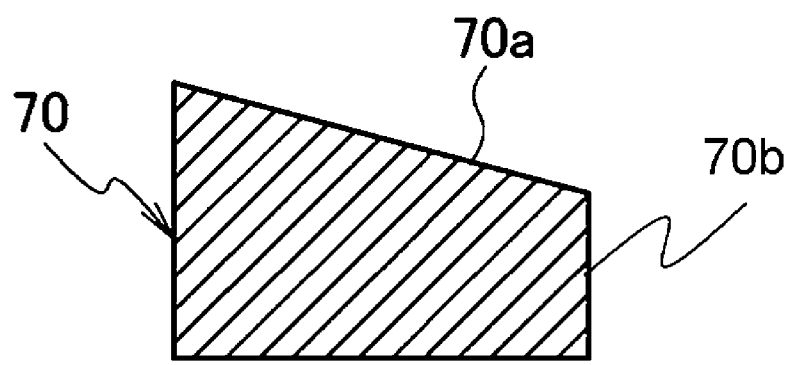
FIG. 8C is a sectional view, corresponding to the VIIIA-VIIIA sectional view in FIG. 8A, illustrating a protruding part according to a fourth modification of the first exemplary embodiment of the present disclosure.

In addition, pressure-receiving part 70 may be configured to have a shape in which surface 70a is inclined as illustrated in a sectional view in FIG. 8C.

As described above, electrochemical measurement device 20 according to the present exemplary embodiment includes substrate (base part) 30, and sample placement part (placement part) 31 which is provided to substrate (base part) 30 and on which a biological sample (object to be measured) is placed. Electrochemical measurement device 20 also includes first ring electrode 41 (electrode part 40) provided near sample placement part 31 on substrate (base part) 30, wiring pattern 51 (wiring part 50) provided on surface 30a of substrate (base part) 30 and electrically connected to first ring electrode 41 (electrode part 40), and insulator 60 that covers wiring pattern 51 (wiring part 50).

Further, pressure-receiving part (protruding part) 70 is provided on substrate (base part) 30 of electrochemical measurement device 20 so as to protrude past insulator 60.

According to this configuration, in forming electrochemical measurement apparatus 10 using electrochemical measurement device 20, insulator 60 is prevented from being pressed by pin 80, whereby insulator 60 can be prevented from being damaged. Accordingly, electrochemical measurement device 20 capable of measuring more accurately can be obtained.

In addition, in the present exemplary embodiment, a portion of first ring electrode 41 is exposed through opening 61a formed in first insulating layer 61. Specifically, a region (surface 41a and lateral surface 41d) of first ring electrode 41 exposed from substrate 30 is covered by first insulating layer 61. A portion (a portion of surface 41a) of the region of first ring electrode 41 exposed from substrate 30 is exposed through opening 61a.

Due to this configuration, first ring electrode 41 is in contact with the culture solution only at first electrode exposed part 41b, by which reduction in noise can be achieved. Thus, more accurate electrochemical measurement can be implemented.

In addition, in the present exemplary embodiment, pressure-receiving part (protruding part) 70 is formed to surround sample placement part 31. Therefore, a region where sample placement part 31 communicates with the peripheral portion of substrate 30 can be reduced with pressure-receiving part 70 being pressed by pin 80. Consequently, resin flow toward sample placement part 31 can be suppressed.

In addition, first ring electrode 41 is formed into a ring shape, and pressure-receiving part (protruding part) 70 is formed such that lateral surface 70b facing electrode part 40 is along lateral surface 41d of electrode part 40 facing pressure-receiving part 70. According to this configuration, pressure-receiving part (protruding part) 70 can be formed on a minimum necessary portion, whereby pressure-receiving part (protruding part) 70 can be more efficiently formed with simple configuration.

If pressure-receiving part (protruding part) 70 is formed from a material same as the material for insulator 60, the manufacturing process can be simplified, and if formed from a material different from the material for insulator 60, pressure-receiving part (protruding part) 70 can be formed from more optimum material according to usage.

Further, by using electrochemical measurement device 20 described above, electrochemical measurement apparatus 10 is formed by surrounding electrochemical measurement device 20 by peripheral wall part 11 so that the surface of electrochemical measurement device 20 on which sample placement part 31 is formed becomes bottom surface 10a. Accordingly, electrochemical measurement apparatus 10 capable of measuring more accurately can be obtained.

Second Exemplary Embodiment

Electrochemical measurement device 20A according to the present exemplary embodiment is basically almost similar in configuration to electrochemical measurement device 20 described in the first exemplary embodiment. The configuration of electrochemical measurement device 20A will be described with reference to a top view in FIG. 9.

Figure 9:
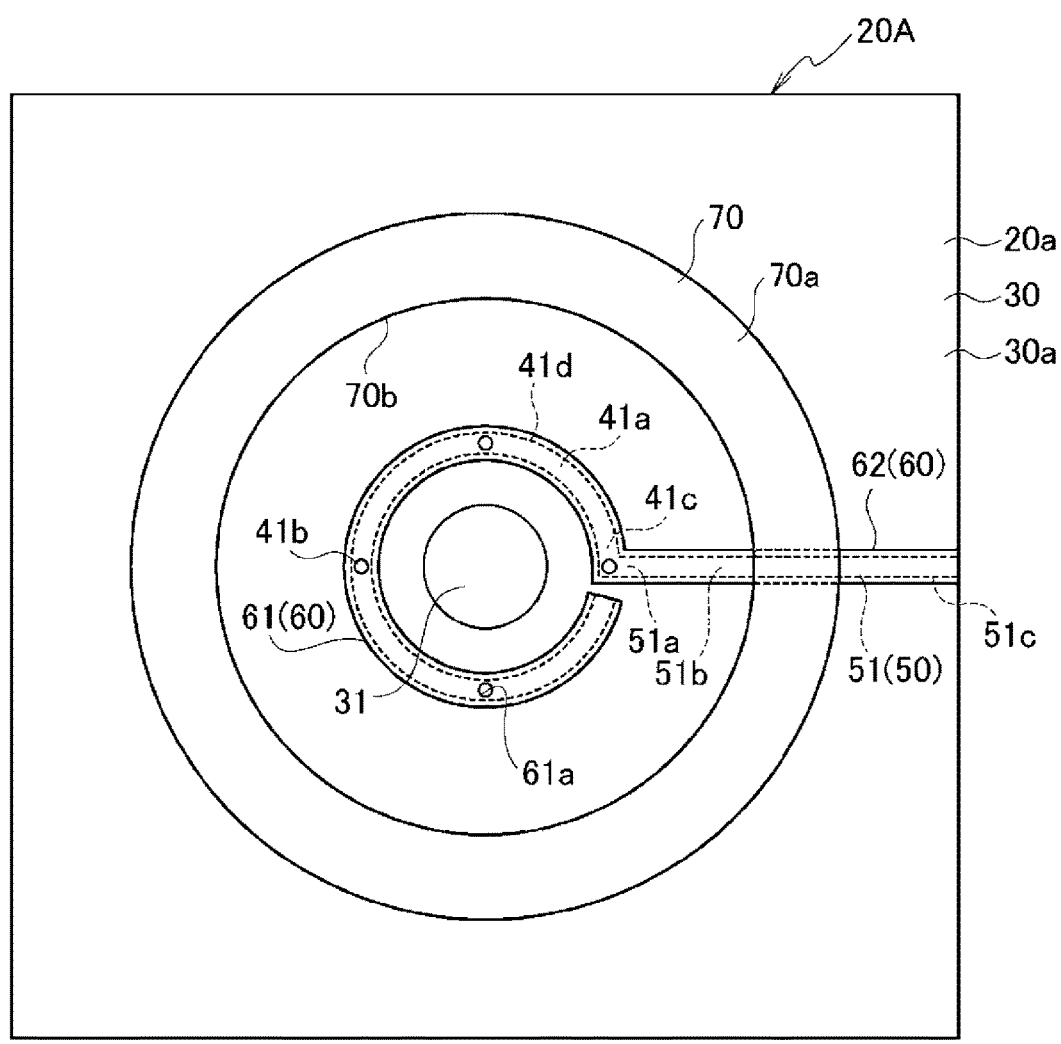
FIG. 9 is a top view illustrating an electrochemical measurement device according to a second exemplary embodiment of the present disclosure.

As illustrated in FIG. 9, electrochemical measurement device 20A according to the present exemplary embodiment includes substrate (base part) 30, and sample placement part (placement part) 31 which is provided to substrate (base part) 30 and on which a biological sample (object to be measured) is placed. Electrochemical measurement device 20A also includes first ring electrode 41 (electrode part 40) provided near sample placement part 31 on substrate (base part) 30, wiring pattern 51 (wiring part 50) provided on surface 30a of substrate (base part) 30 and electrically connected to first ring electrode 41 (electrode part 40), and insulator 60 that covers wiring pattern 51 (wiring part 50).

Further, pressure-receiving part (protruding part) 70 is provided on substrate (base part) 30 of electrochemical measurement device 20A so as to protrude past insulator 60.

Here, in electrochemical measurement device 20A according to the present exemplary embodiment, pressure-receiving part (protruding part) 70 is formed throughout the entire circumference. That is, pressure-receiving part (protruding part) 70 is formed to have substantially an O shape without having a gap in a plan view. Pressure-receiving part (protruding part) 70 is disposed to intersect second insulating layer 62 that covers wiring pattern 51, and a portion of second insulating layer 62 is covered by pressure-receiving part (protruding part) 70. In pressure-receiving part (protruding part) 70, layer 71 facing substrate 30 on at least a region where pressure-receiving part (protruding part) 70 covers second insulating layer 62 is made of a material having elasticity.

When peripheral wall part 11 is formed around substrate 30, using electrochemical measurement device 20A described above, in the manner described in the first exemplary embodiment, electrochemical measurement apparatus 10 having well 12 for holding solution (culture solution, or the like) can be obtained.

According to the present exemplary embodiment, the operation and effect similar to those in the first exemplary embodiment can also be obtained.

In addition, in the present exemplary embodiment, a portion of second insulating layer 62 is covered by pressure-receiving part (protruding part) 70, and layer 71 of pressure-receiving part (protruding part) 70 facing substrate 30 on at least the region where pressure-receiving part (protruding part) 70 covers second insulating layer 62 is formed from a material having elasticity such as polyimide.

According to this configuration, although insulator 60 is pressed by pin through pressure-receiving part (protruding part) 70 in forming electrochemical measurement apparatus 10 using electrochemical measurement device 20A, the region of pressure-receiving part (protruding part) 70 pressing insulator 60 is formed from a material having elasticity, whereby pressure from pin 80 can be eased by pressure-receiving part (protruding part) 70. Consequently, insulator 60 can be prevented from being damaged.

Note that the present exemplary embodiment can be applied to the pressure-receiving part illustrated in FIGS. 6 and 7. Specifically, pressure-receiving part 70 illustrated in FIGS. 6 and 7 can be configured to have no gap.

Third Exemplary Embodiment

Electrochemical measurement device 20B according to the present exemplary embodiment is basically almost similar in configuration to electrochemical measurement device 20 described in the first exemplary embodiment. The configuration of electrochemical measurement device 20B will be described with reference to a top view in FIG. 10 and a sectional view in FIG. 11. FIG. 11 is a sectional view taken along line XI-XI in FIG. 10.

Figure 10:
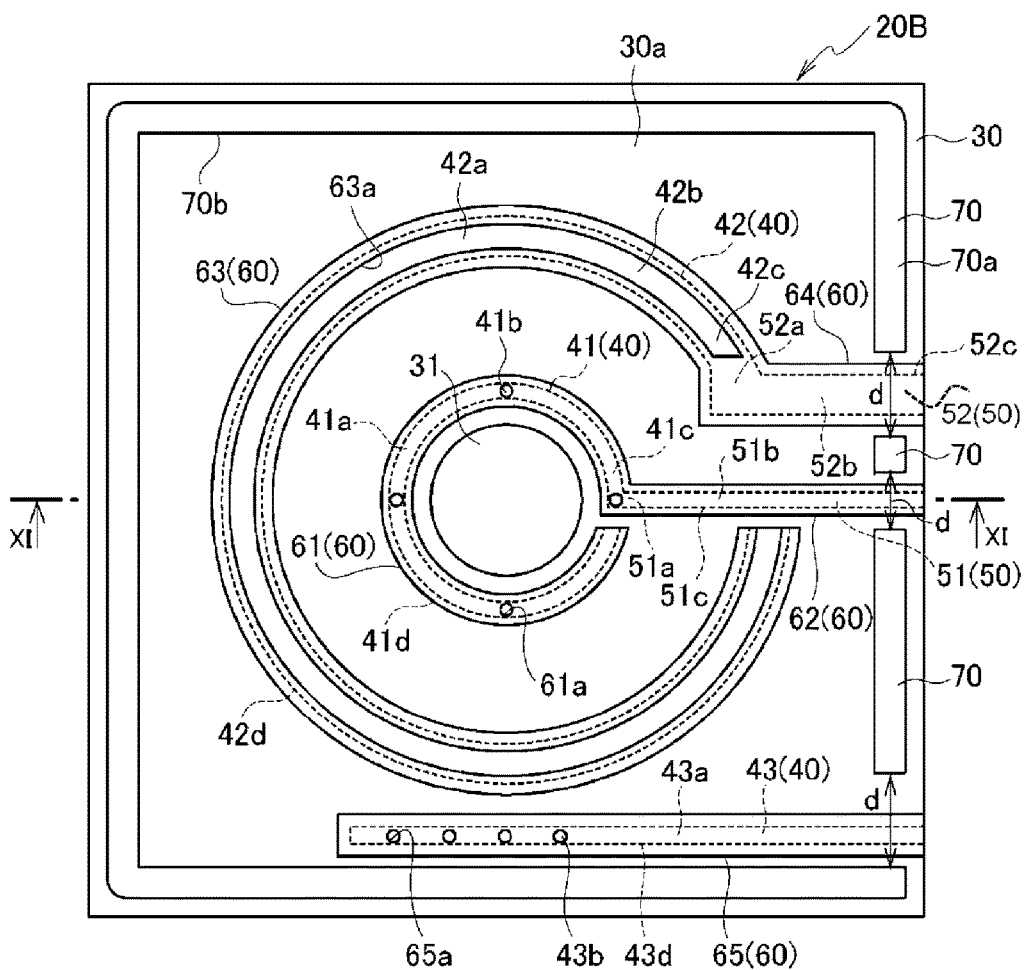
FIG. 10 is a top view illustrating an electrochemical measurement device according to a third exemplary embodiment of the present disclosure.
Figure 11:
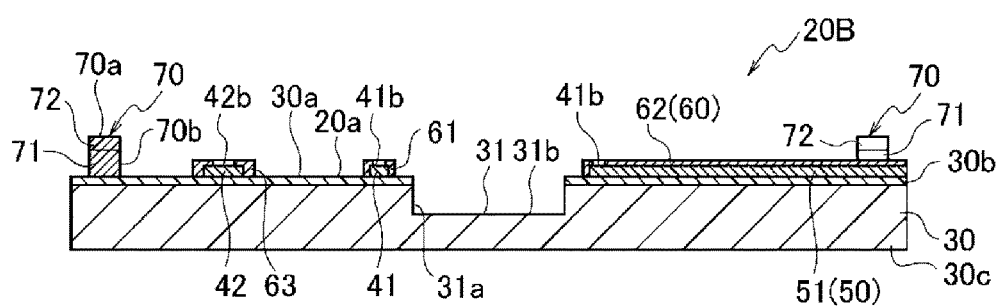
FIG. 11 is a sectional view taken along line XI-XI in FIG. 10.

As illustrated in FIGS. 10 and 11, electrochemical measurement device 20B according to the present exemplary embodiment includes substrate (base part) 30, and sample placement part (placement part) 31 which is provided to substrate (base part) 30 and on which a biological sample (object to be measured) is placed. Electrochemical measurement device 20B also includes first ring electrode 41 (electrode part 40) provided near sample placement part 31 on substrate (base part) 30, wiring pattern 51 (wiring part 50) provided on surface 30a of substrate (base part) 30 and electrically connected to first ring electrode 41 (electrode part 40), and insulator 60 that covers wiring pattern 51 (wiring part 50).

Further, pressure-receiving part (protruding part) 70 is provided on substrate (base part) 30 of electrochemical measurement device 20B so as to protrude past insulator 60.

In electrochemical measurement device 20B according to the present exemplary embodiment, counter electrode 42 serving as electrode part 40 is provided on substrate 30.

Counter electrode 42 serving as electrode part 40 has substantially a C shape in a plan view, and is provided on surface 30a of substrate 30 to surround first ring electrode 41. It is preferable that counter electrode 42 is also concentrically arranged around sample placement part 31.

Counter electrode 42 can be made of noble metals such as platinum, gold, or silver, for example. In addition, counter electrode 42 can be made of a material popularly used as an electrode material for a battery, such as carbon or lithium cobalt oxide. That is, the material for counter electrode 42 can also be selected, as appropriate, in consideration of a composition of culture solution or voltage and current required for the measurement.

Electrochemical measurement device 20B also includes wiring pattern 52 serving as wiring part 50 electrically connected to counter electrode 42.

In the present exemplary embodiment, one end 52a of wiring pattern 52 is connected to one end 42c of counter electrode 42 formed into a C shape. Wiring pattern 52 linearly extends from one end 52a so as to be almost parallel to wiring pattern 51. Note that the shape of wiring pattern 52 is also not limited to be linear.

Electrochemical measurement device 20B also includes fourth insulating layer 64 serving as insulator 60 for covering a region (surface 52b and lateral surface 52c) of wiring pattern 52 exposed from substrate 30.

Specifically, in the present exemplary embodiment, insulator 60 has third insulating layer 63 for covering a region (surface 42a and lateral surface 42d) of counter electrode 42 exposed from substrate 30 and fourth insulating layer 64 for covering the region (surface 52b and lateral surface 52c) of wiring pattern 52 exposed from substrate 30, as well as first insulating layer 61 and second insulating layer 62. In addition, in the present exemplary embodiment, third insulating layer 63 and fourth insulating layer 64 are integrally formed.

Third insulating layer 63 is formed on surface 30a of substrate 30 so as to cover counter electrode 42, and made of silicon dioxide, silicon nitride, organic compound, or the like to insulate counter electrode 42 and culture solution from each other.

Similarly, fourth insulating layer 64 is formed on surface 30a of substrate 30 so as to cover wiring pattern 52, and made of silicon dioxide, silicon nitride, organic compound, or the like to insulate wiring pattern 52 and culture solution from each other.

In addition, in the present exemplary embodiment, opening 63a is formed on third insulating layer 63. The region of counter electrode 42 exposed from substrate 30, that is, a portion (a portion of surface 42a in the present exemplary embodiment) of the region (surface 42a and lateral surface 42d) exposed from substrate 30 when counter electrode 42 is not covered by third insulating layer 63, is exposed through opening 63a.

Specifically, counter electrode 42 has counter electrode exposed part 42b exposed from opening 63a in third insulating layer 63. According to this configuration, counter electrode 42 is in contact with culture solution at counter electrode exposed part 42b. Note that opening 63a in third insulating layer 63 can be formed to have a circular shape or a polygonal shape, for example (in FIG. 10, opening 63a which is circumferentially curved is illustrated). Notably, it is possible not to form an insulating layer on counter electrode 42 or wiring pattern 52.

It is preferable that counter electrode exposed part 42b is arranged so that a physicochemical change around a biological sample does not affect the electrochemical reaction occurring on counter electrode exposed parts 42b. For example, the distance between an end of counter electrode exposed part 42b and an end of sample placement part 31 is not less than 400 μm.

In addition, counter electrode exposed part 42b is preferably arranged such that an effect caused by overlapping of a diffusion layer formed by counter electrode exposed part 42b and a diffusion layer formed by first electrode exposed part 41b is not exerted on the electrochemical reaction occurring on first electrode exposed part 41b and counter electrode exposed part 42b. For example, the distance between an end of counter electrode exposed part 42b and an end of first electrode exposed part 41b is not less than 400 μm.

It is also desirable that the end of counter electrode exposed part 42b and the biological sample is not less than 400 μm so as to prevent the physicochemical state change around the biological sample from being affected. In addition, it is preferable that an area of counter electrode exposed part 42b is not less than the total area of first electrode exposed parts 41b.

Counter electrode 42 is not necessarily formed on substrate 30. If counter electrode 42 is not provided on substrate 30, a bulk body containing a material popularly used as an electrode material for a battery, such as: noble metal including platinum, gold, or silver; carbon; or lithium cobalt oxide, is inserted into culture solution as counter electrode 42 to perform measurement. Furthermore, counter electrode 42 is not necessary, and may not be provided.

Electrochemical measurement device 20B according to the present exemplary embodiment also has blank electrode 43 provided on substrate 30 for reference measurement which is not affected by the activity of the biological sample.

Blank electrode 43 are covered by fifth insulating layer 65, having opening 65a formed therein, on surface 43a and lateral surface 43d, and has blank electrode exposed part 43b on surface 43a thereof.

Blank electrode 43 is made of the material same as the material for first ring electrode 41. The total area of blank electrode exposed part 43b is equal to the total area of first electrode exposed parts 41b. In addition, it is preferable that blank electrode exposed part 43b is arranged so that a physicochemical change around the biological sample does not affect the electrochemical reaction occurring on blank electrode exposed part 43b. For example, the distance between the end of blank electrode exposed part 43b closest to sample placement part 31 and the end of sample placement part 31 is not less than 400 μm.

In addition, blank electrode exposed part 43b is preferably arranged such that an effect caused by overlapping of a diffusion layer formed by blank electrode exposed part 43b and a diffusion layer formed by first electrode exposed part 41b or a diffusion layer formed by counter electrode exposed part 42b is not exerted on the electrochemical reaction occurring on first electrode exposed part 41b, counter electrode exposed part 42b, and blank electrode exposed part 43b. For example, the distance between the end of blank electrode exposed part 43b and the end of first electrode exposed part 41b, which are closest to each other, is 6.5 times or more of the sum of a half of the diameter of first electrode exposed part 41b and a half of the diameter of blank electrode exposed part 43b. In addition, if there are a plurality of blank electrode exposed parts 43b, the distance between adjacent blank electrode exposed parts 43b is preferably 6.5 times or more of the dimension of blank electrode exposed part 43b. Herein, the dimension of blank electrode exposed part 43b indicates a diameter of a minimum circle which includes blank electrode exposed part 43b. For example, if blank electrode exposed part 43b is a circle, the dimension of blank electrode exposed part 43b is a diameter. If blank electrode exposed part 43b is a rectangle, the dimension of blank electrode exposed part 43b is the length of a diagonal.

Note that the first to fifth insulating layers may have the same insulating layer. That is, an insulator may be provided between first ring electrode 41, counter electrode 42, and blank electrode 43. Due to the configuration in which the insulator have the same insulating layer, man-hours in the manufacturing process can be reduced.

Figure 13:
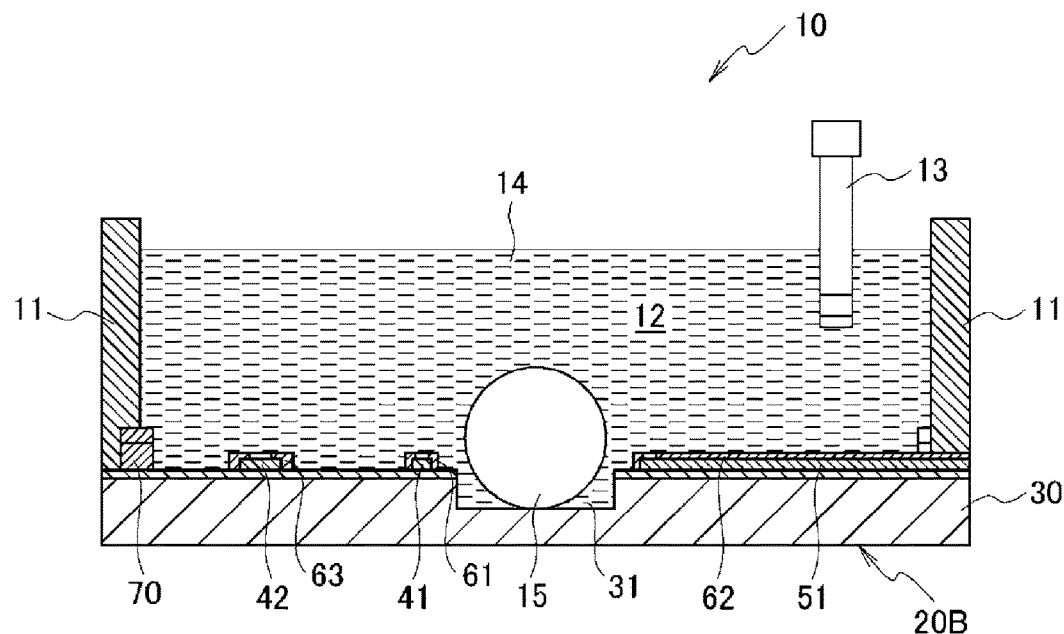
FIG. 13 is a sectional view schematically illustrating a use state of the electrochemical measurement apparatus according to the present disclosure.

While reference electrode 13 is inserted into culture solution 14 in FIG. 13, reference electrode 13 may be provided on substrate 30. This is also applied to the first and second exemplary embodiments described above.

Ag/AgCl, Au, etc. is used as the material for reference electrode 13. Reference electrode 13 is preferably arranged such that an effect caused by overlapping of a diffusion layer formed by reference electrode 13 and diffusion layers formed respectively by first electrode exposed part 41b, counter electrode exposed part 42b, and blank electrode exposed part 43b is not exerted on the electrochemical reaction occurring on first electrode exposed part 41b, counter electrode exposed part 42b, and blank electrode exposed part 43b. For example, the distance between an end of reference electrode 13 and ends of first electrode exposed part 41b, counter electrode exposed part 42b, and blank electrode exposed part 43b is not less than 400 μm.

In addition, first ring electrode 41 and blank electrode 43 are individually connected to measurement amplifiers. A potential difference between first ring electrode 41 or blank electrode 43 and reference electrode 13 and current in the electrochemical reaction detected on first ring electrode 41 and blank electrode 43 are individually measured.

On substrate (base part) 30 of electrochemical measurement device 20B, pressure-receiving part (protruding part) 70 is provided to surround all of electrode exposed parts (first electrode exposed parts 41b, counter electrode exposed part 42b, and blank electrode exposed parts 43b) formed on substrate (base part) 30.

In addition, in the present exemplary embodiment, pressure-receiving part 70 also has a disconnected part, and gap d is formed on the disconnected p art.

Note that, in the present exemplary embodiment, it is also possible not to form a disconnected part on pressure-receiving part 70 as in the second exemplary embodiment.

When peripheral wall part 11 is formed around substrate 30, using electrochemical measurement device 20B described above, in the manner described in the first exemplary embodiment, electrochemical measurement apparatus 10 having well 12 for holding solution (culture solution, or the like) can be obtained.

According to the present exemplary embodiment described above, the operation and effect similar to those in the first exemplary embodiment can also be obtained.

Fourth Exemplary Embodiment

Electrochemical measurement device 20C according to the present exemplary embodiment is basically almost similar in configuration to electrochemical measurement device 20B described in the third exemplary embodiment. The configuration of electrochemical measurement device 20C will be described with reference to a top view in FIG. 12.

Figure 12:
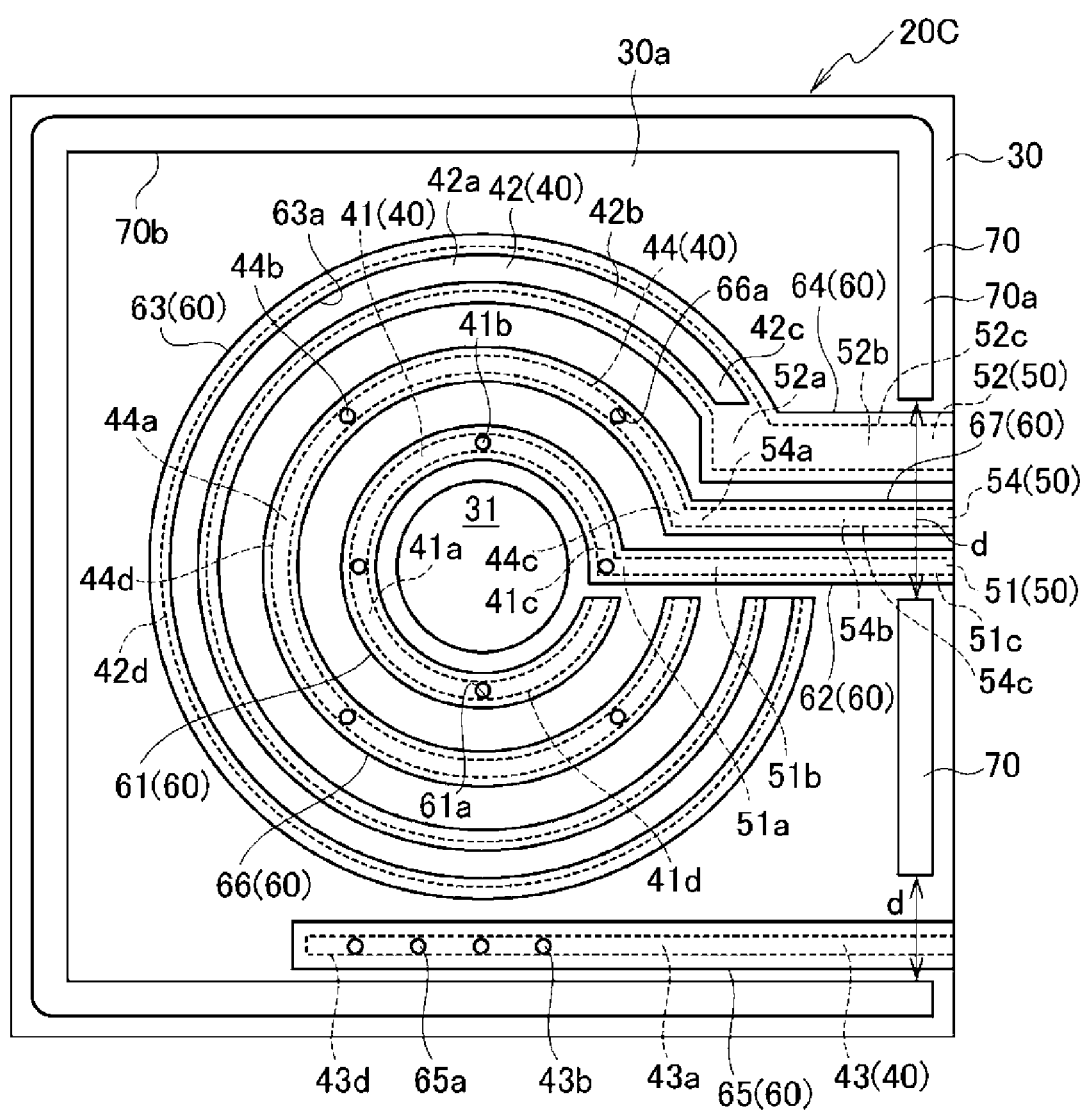
FIG. 12 is a top view illustrating an electrochemical measurement device according to a fourth exemplary embodiment of the present disclosure.

As illustrated in FIG. 12, electrochemical measurement device 20C according to the present exemplary embodiment includes substrate (base part) 30, and sample placement part (placement part) 31 which is provided to substrate (base part) 30 and on which a biological sample (object to be measured) is placed. Electrochemical measurement device 20C also includes first ring electrode 41 (electrode part 40) provided near sample placement part 31 on substrate (base part) 30, wiring pattern 51 (wiring part 50) provided on surface 30a of substrate (base part) 30 and electrically connected to first ring electrode 41 (electrode part 40), and insulator 60 that covers wiring pattern 51 (wiring part 50).

In addition, electrode part 40 has first ring electrode 41, counter electrode 42, and blank electrode 43.

Further, pressure-receiving part (protruding part) 70 is provided on substrate (base part) 30 of electrochemical measurement device 20C so as to protrude past insulator 60.

Herein, in electrochemical measurement device 20C according to the present exemplary embodiment, second ring electrode 44 is formed on substrate 30 so as to surround first ring electrode 41.

That is, second ring electrode 44 is formed between first ring electrode 41 and counter electrode 42.

Therefore, in the present exemplary embodiment, the distance between second electrode exposed part 44b and sample placement part 31 is larger than the distance between first electrode exposed part 41b and sample placement part 31.

Due to the configuration in which second ring electrode 44 is provided on the outside of first ring electrode 41, electrochemical measurement of a biological sample can be carried out at different distances from sample placement part 31, whereby an activity condition of the biological sample depending on the distance from the biological sample can be monitored.

Second ring electrode 44 serving as electrode part 40 has substantially a C shape in a plan view, and is provided on surface 30a of substrate 30 to surround first ring electrode 41. It is preferable that second ring electrode 44 is also concentrically arranged around sample placement part 31.

Second ring electrode 44 can be made of noble metals such as platinum, gold, or silver, for example. In addition, second ring electrode 44 can be made of a material popularly used as an electrode material for a battery, such as carbon or lithium cobalt oxide. That is, the material for second ring electrode 44 can also be selected, as appropriate, in consideration of a composition of culture solution or voltage and current required for the measurement. Electrochemical measurement device 20C also includes wiring pattern 54 serving as wiring part 50 electrically connected to second ring electrode 44 serving as electrode part 40.

In the present exemplary embodiment, one end 54a of wiring pattern 54 is connected to one end 44c of second ring electrode 44 formed into a C shape. Wiring pattern 54 linearly extends from one end 54a so as to be almost parallel to wiring pattern 51. Note that the shape of wiring pattern 54 is also not limited to be linear.

Electrochemical measurement device 20C also includes insulator 60 for covering a region (surface 54b and lateral surface 54c) of wiring part 50 exposed from substrate 30.

Insulator 60 has sixth insulating layer 66 for covering a region (surface 44a and lateral surface 44d) of second ring electrode 44 exposed from substrate 30 and seventh insulating layer 67 for covering the region (surface 54b and lateral surface 54c) of wiring pattern 54 exposed from substrate 30, as well as first insulating layer 61 to fifth insulating layer 65. In addition, in the present exemplary embodiment, sixth insulating layer 66 and seventh insulating layer 67 are integrally formed. Specifically, the region of second ring electrode 44 exposed from substrate 30 and the region of wiring pattern 54 exposed from substrate 30 are covered by single insulator (sixth insulating layer 66 and seventh insulating layer 67).

Sixth insulating layer 66 is formed on surface 30a of substrate 30 so as to cover second ring electrode 44, and made of silicon dioxide, silicon nitride, organic compound, or the like to insulate second ring electrode 44 and culture solution from each other.

Similarly, seventh insulating layer 67 is formed on surface 30a of substrate 30 so as to cover wiring pattern 54, and made of silicon dioxide, silicon nitride, organic compound, or the like to insulate wiring pattern 54 and culture solution from each other.

In addition, in the present exemplary embodiment, opening 66a is formed on sixth insulating layer 66. The region of second ring electrode 44 exposed from substrate 30, that is, a portion (a portion of surface 44a in the present exemplary embodiment) of the region (surface 44a and lateral surface 44d) exposed from substrate 30 when second ring electrode 44 is not covered by sixth insulating layer 66, is exposed through opening 66a.

Specifically, second ring electrode 44 has second electrode exposed part 44b exposed from opening 66a in sixth insulating layer 66. According to this configuration, second ring electrode 44 is in contact with culture solution at second electrode exposed part 44b. Note that opening 66a in sixth insulating layer 66 can be formed to have a circular shape or a polygonal shape, for example (in FIG. 12, circular opening 66a is illustrated).

Note that the first to seventh insulating layers may have the same insulating layer. That is, an insulator may be provided between first ring electrode 41, counter electrode 42, blank electrode 43, and second ring electrode 44. Due to the configuration in which the insulator has the same insulating layer, man-hours in the manufacturing process can be reduced.

Due to the configuration in which second ring electrode 44 is covered by sixth insulating layer 66 so that second ring electrode 44 is in contact with the culture solution only at second electrode exposed part 44b, reduction in noise can be achieved, whereby more accurate electrochemical measurement can be implemented.

In addition, in the present exemplary embodiment, wiring pattern 54 drawn from second ring electrode 44 is covered by seventh insulating layer 67, by which the contact between wiring pattern 54 and the culture solution can be prevented. According to this configuration, current detection on an unnecessary position (unexpected position) based on an electrochemical reaction can be reduced.

If electrochemical measurement is carried out by bringing second ring electrode 44 entirely in contact with the culture solution without being covered by sixth insulating layer 66, nonfaradaic current being noise increases with an increase in the electrode area, by which accurate electrochemical measurement cannot be carried out in some cases. Further, in measurement of dissolved oxygen in culture solution due to respiration activity of a fertilized egg, for example, an amount of oxygen consumed in response to an electrochemical reaction increases with an increase in the electrode area, which might affect the oxygen concentration near the fertilized egg, and thus, the respiration activity cannot accurately be measured in some cases.

Therefore, it is preferable that the area of second electrode exposed part 44b is set to be 500 $\mu m^2$ or less so that nonfaradaic current being measurement noise is reduced or the influence on the oxygen concentration near the fertilized egg caused by the consumption of oxygen in response to the electrochemical reaction is reduced.

In addition, in the present exemplary embodiment, a plurality of second electrode exposed parts 44b is arranged on second ring electrode 44 to enable multidirectional measurement of a biological sample. In this case, it is preferable that second electrode exposed parts 44b are arranged to be equally distant from sample placement part 31. With this configuration, a physicochemical state change such as an oxygen concentration around a biological sample can be easily measured by electrochemical measurement, regardless of imbalance in the activity of the biological sample.

In the present exemplary embodiment, four second electrode exposed parts 44b are provided on second ring electrode 44. Four second electrode exposed parts 44b are equally spaced at 90 degrees around sample placement part 31. Note that the number of second electrode exposed parts 44b is not limited to four. For example, eight second exposed electrode parts 44b can be formed on second ring electrode 44. In this case, they are equally spaced at 45 degrees around sample placement part 31.

In addition, second electrode exposed parts 44b are preferably arranged such that an effect caused by overlapping of diffusion layers formed by respective second electrode exposed parts 44b is not exerted on the electrochemical reaction occurring on second electrode exposed parts 44b. For example, the distance between two adjacent second electrode exposed parts 44b is preferably 6.5 times or more of the dimension of second electrode exposed part 44b.

In addition, for the above-mentioned reason, it is preferable that the distance between an end of first electrode exposed part 41b and an end of second electrode exposed part 44b is also 6.5 times or more of the dimension of second electrode exposed part 44b. For example, second electrode exposed part 44b on second ring electrode 44 can be provided between two adjacent first electrode exposed parts 41b on first ring electrode 41 as viewed from sample placement part 31.

Notably, second electrode exposed part 44b on second ring electrode 44 is preferably arranged so that the distance between second electrode exposed part 44b and blank electrode exposed part 43b is 6.5 times or more of the sum of a half of the dimension of second electrode exposed part 44b and a half of the dimension of blank electrode exposed part 43b, and such that the distance between second electrode exposed part 44b and counter electrode exposed part 42b or reference electrode 13 is not less than 400 µm. Herein, the dimension of second electrode exposed part 44b indicates a diameter of a minimum circle which includes second electrode exposed part 44b. For example, if second electrode exposed part 44b is a circle, the dimension of second electrode exposed part 44b is a diameter. If second electrode exposed part 44b is a rectangle, the dimension of second electrode exposed part 44b is the length of a diagonal.

In addition, second electrode exposed parts 44b are arranged to be equally distant from the center of sample placement part 31. With the configuration in which second electrode exposed parts 44b are arranged to be equally distant from sample placement part 31, a physicochemical state change such as an oxygen concentration around a biological sample can be easily measured by electrochemical measurement, regardless of imbalance in the activity of the biological sample.

The number and total area of second electrode exposed parts 44b on second ring electrode 44 are preferably the same as the number and total area of first electrode exposed parts 41b on first ring electrode 41.

In the present exemplary embodiment, first electrode exposed parts 41b have the same area. In addition, second electrode exposed parts 44b also have the same area.

While second ring electrode 44 has a ring shape having a gap, second ring electrode 44 may have a ring shape with no gap. However, if wiring pattern 51 for first ring electrode 41 is formed on surface 30a of substrate 30, second ring electrode 44 preferably has a ring shape having a gap. In this case, wiring pattern 51 for first ring electrode 41 can be provided in the gap of second ring electrode 44. Similarly, counter electrode 42 can be configured to have a ring shape with a gap.

Notably, one or more ring electrodes can further be formed on the outside of second ring electrode 44. When electrode exposed parts are formed on positions at different distances from sample placement part 31, the electrochemical measurement according to the distance from the biological sample can be carried out in more detail.

First ring electrode 41 and second ring electrode 44 are connected to respective measurement amplifiers so that currents flowing through both electrodes can be simultaneously measured. Thus, an amount of dissolved oxygen or the like which is the physicochemical change occurring around the biological sample can be simultaneously measured.

In addition, first ring electrode 41 and second ring electrode 44 may be connected to a single measurement amplifier using a switch or a relay to carry out the measurement in a time-division manner. When a plurality of ring electrodes is connected to a single measurement amplifier using a switching circuit including a switch or a relay, the apparatus can be made compact.

However, if the switching circuit is used, it is desirable to use a switch or a relay operating at high speed. When a switch or the like operating at high speed is used, the electrochemical measurement around the biological sample can accurately be carried out in response to the temporal change in an amount of dissolved oxygen or the like.

On substrate (base part) 30 of electrochemical measurement device 20C, pressure-receiving part (protruding part) 70 is provided to surround all of electrode exposed parts (first electrode exposed parts 41b, counter electrode exposed part 42b, blank electrode exposed parts 43b, and second electrode exposed parts 44b) formed on substrate (base part) 30.

In addition, in the present exemplary embodiment, pressure-receiving part 70 also has a disconnected part, and gap d is formed on the disconnected part.

Note that, in the present exemplary embodiment, it is also possible not to form a disconnected part on pressure-receiving part 70 as in the second exemplary embodiment.

When peripheral wall part 11 is formed around substrate 30, using electrochemical measurement device 20C described above, in the manner described in the first exemplary embodiment, electrochemical measurement apparatus 10 having well 12 for holding solution (culture solution, or the like) can be obtained.

According to the present exemplary embodiment described above, the operation and effect similar to those in the first exemplary embodiment can also be obtained.

Next, the operation of electrochemical measurement apparatus 10 for a biological sample will be described with reference to FIG. 13. FIG. 13 is a sectional view schematically illustrating a use state of electrochemical measurement apparatus 10 according to the present disclosure.

FIG. 13 illustrates electrochemical measurement apparatus 10 formed by using electrochemical measurement device 20B described in the third exemplary embodiment. However, even when an electrochemical measurement apparatus is formed by using the electrochemical measurement devices described in other exemplary embodiments, the apparatus basically operates in the same manner.

Examples of biological sample 15 include a cell, a tissue, and a fertilized egg. A concentration gradient of active oxygen or metabolic substances from biological sample 15 is radially formed. Hereinafter, a fertilized egg is used as biological sample 15.

Electrochemical measurement device 20B has peripheral wall part 11 formed on the peripheral portion thereof. Therefore, well 12 into which culture solution 14 is injected is formed in a region surrounded by substrate 30 and peripheral wall part 11.

Now, culture solution 14 containing a fertilized egg is injected into well 12 as biological sample 15, and the fertilized egg is placed on sample placement part 31.

Then, reference electrode 13 is inserted into culture solution 14. Note that, if reference electrode 13 is provided on substrate 30, it does not need to be inserted. In addition, if counter electrode 42 is not provided on substrate 30, a counter electrode is inserted into the culture solution. Notably, counter electrode 42 is not necessary, and may not be inserted into the culture solution.

With the potential of reference electrode 13 being a reference, a potential is applied to first ring electrode 41, and a current value detected on first ring electrode 41 in response to the electrochemical reaction is measured. Through the measurement of the current value, the amount of dissolved oxygen in culture solution 14 can be measured. The amount of dissolved oxygen is associated with an amount of oxygen consumed as a result of the activity of biological sample 15 such as a fertilized egg. Therefore, the activity state of biological sample 15 such as a fertilized egg can be obtained by measuring the amount of dissolved oxygen.

While the preferable exemplary embodiments of the present disclosure have been described above, the present disclosure is not limited to the above-mentioned exemplary embodiments, and various modifications are possible.

For example, a configuration can be made by combining the components described in the above-mentioned exemplary embodiments as appropriate.

In addition, detailed specifications (shape, size, layout, etc.) of the electrode part, the insulator, and other components can be changed as appropriate.

What is claimed is:

1. An electrochemical measurement apparatus comprising:
    a base part;
    a placement part on which an object to be measured is placed, the placement part being provided to the base part;
    an electrode part provided near the placement part on the base part;
    a wiring part provided to a surface of the base part and electrically connected to the electrode part;
    an insulator that covers the electrode part;
    a protruding part provided on an upper surface of the base part so as to protrude above an upper surface of the insulator; and
    a peripheral wall part that surrounds the placement part; wherein
    the protruding part has an upper surface, an inner side surface connected to the upper surface of the protruding part, and an outer side surface connected to the upper surface of the protruding part and being opposite to the inner side surface, the inner surface facing the electrode part,
    the upper surface of the base part has a portion extending beyond the outer side surface of the protruding part,
    the peripheral wall part is provided on the portion of the upper surface of the base part,
    the electrode part is exposed through an opening formed in the insulator,
    the upper surface of the protruding part has an inner portion and an outer portion, wherein the inner portion is connected to the inner side surface and the outer portion is connected to the outer side surface,
    the peripheral wall part protrudes over the upper surface of the protruding part, and is disposed directly on the outer portion of the upper surface of the protruding part, and
    the inner portion of the upper surface of the protruding part is exposed from the peripheral wall part.

2. The electrochemical measurement apparatus according to claim 1, wherein the protruding part is formed on an either side of the wiring part.

3. The electrochemical measurement apparatus according to claim 1, wherein the protruding part is formed to surround the placement part.

4. The electrochemical measurement apparatus according to claim 1, wherein
    the electrode part is formed into a ring shape, and
    the protruding part is formed so that a surface of the protruding part facing the electrode part is along a surface of the electrode part facing the protruding part.

5. The electrochemical measurement apparatus according to claim 1, wherein the protruding part includes a portion formed from a material same as a material for the insulator.

6. The electrochemical measurement apparatus according to claim 1, wherein the protruding part includes a portion formed from a material different from a material for the insulator.

7. The electrochemical measurement apparatus according to claim 1, wherein the peripheral wall part includes a portion formed from a material different of a material for the protruding part.

8. The electrochemical measurement apparatus according to claim 1, wherein the protruding part is apart from the electrode part.

* * * * *